US00PP20566P2

(12) United States Plant Patent
Green, Jr.

(10) Patent No.: US PP20,566 P2
(45) Date of Patent: Dec. 15, 2009

(54) ***CAMELLIA* PLANT NAMED 'GREEN 97-039'**

(50) Latin Name: *Camellia sasanqua*
Varietal Denomination: Green 97-039

(76) Inventor: Robert M. Green, Jr., 415 Maple St., Fairhope, AL (US) 36532

( * ) Notice: Subject to any disclaimer, the term of this patent is extended or adjusted under 35 U.S.C. 154(b) by 0 days.

(21) Appl. No.: 12/217,735

(22) Filed: Jul. 7, 2008

(51) Int. Cl.
*A01H 5/00* (2006.01)

(52) U.S. Cl. ..... Plt./243
(58) Field of Classification Search ..... Plt./243
See application file for complete search history.

*Primary Examiner*—Annette H Para
(74) *Attorney, Agent, or Firm*—C. A. Whealy

(57) ABSTRACT

A new and distinct cultivar of *Camellia* plant named 'Green 97-039', characterized by its upright plant habit; vigorous growth habit; freely branching habit; freely flowering habit; relatively long flowering period; and double white-colored flowers with magenta-colored margins.

2 Drawing Sheets

Botanical designation: *Camellia sasanqua.*
Cultivar denomination: 'Green 97-039'.

BACKGROUND OF THE INVENTION

The present Invention relates to a new and distinct cultivar of *Camellia*, botanically known as *Camellia sasanqua*, and hereinafter referred to by the name 'Green 97-039'.

The new *Camellia* is a product of a planned breeding program conducted by the Inventor in Fairhope, Ala. The objective of the breeding program is to create new vigorous and freely flowering *Camellia* cultivars having unique and attractive flower color and flower for an extended period of time.

The new *Camellia* originated from an open-pollination in 1997, in Fairhope, Ala., of *Camellia sasanqua* 'Mine-No-Yuki', not patented, as the female, or seed, parent with an unknown selection of *Camellia sasanqua*, as the male, or pollen, parent. The new *Camellia* was discovered and selected by the Inventor as a flowering plant within the progeny of the stated open-pollination in a controlled outdoor nursery environment in Fairhope, Ala. in November, 2002.

Asexual reproduction of the new *Camellia* by terminal cuttings taken in a controlled greenhouse environment in Fairhope, Ala. since August, 2003, has shown that the unique features of this new *Camellia* are stable and reproduced true to type in successive generations.

SUMMARY OF THE INVENTION

Plants of the new *Camellia* have not been observed under all possible environmental conditions. The phenotype may vary somewhat with variations in environment such as temperature and light intensity without, however, any variance in genotype. The following traits have been repeatedly observed and are determined to be the unique characteristics of 'Green 97-039'. These characteristics in combination distinguish 'Green 97-039' as a new and distinct cultivar of *Camellia*:

1. Upright plant habit.
2. Vigorous growth habit.
3. Freely branching habit.
4. Freely flowering habit.
5. Relatively long flowering period.

6. Double white-colored flowers with magenta-colored margins.

Plants of the new *Camellia* differ from plants of the female parent, 'Mine-No-Yuki', in the following characteristics:

1. Plants of the new *Camellia* are more upright than and not as spreading and open as plants of 'Mine-No-Yuki'.
2. Plants of the new *Camellia* have darker green-colored leaves than plants of 'Mine-No-Yuki'.
3. Plants of the new *Camellia* and 'Mine-No-Yuki' differ in flower color as plants of 'Mine-No-Yuki' do not have magenta-colored margins.

Plants of the new *Camellia* can be compared to the plants of *Camellia sasanqua* 'Cotton Candy', not patented. In side-by-side comparisons conducted in Fairhope, Ala., plants of the new *Camellia* differed from plants of the 'Cotton Candy' in the following characteristics:

1. Plants of the new *Camellia* and 'Cotton Candy' differed in flower color as plants of 'Cotton Candy' had pink-colored flowers.
2. Plants of the new *Camellia* flowered for a longer period of time than plants of 'Cotton Candy'.

BRIEF DESCRIPTION OF THE PHOTOGRAPHS

The accompanying colored photographs illustrate the overall appearance of the new *Camellia*. These photographs show the colors as true as it is reasonably possible to obtain in colored reproductions of this type. Colors in the photographs may differ slightly from the color values cited in the detailed botanical description, which accurately describe the colors of the new *Camellia.*

The photograph on the first sheet comprises a side perspective view of a typical flowering plant of 'Green 97-039' grown in an outdoor nursery.

The photograph on the second sheet is a close-up view of typical flowers of 'Green 97-039'.

DETAILED BOTANICAL DESCRIPTION

The aforementioned photographs and following observations and measurements describe plants grown in Fairhope, Ala. in containers in an outdoor nursery during the autumn and under commercial production conditions. During the production of the plants, day temperatures averaged 24° C. and night temperatures averaged 7° C. Plants were grown under 30% polypropylene shadecloth. Plants used for the photographs were nine years from planting, and plants used for the description were 30 months from planting. In the following description, color references are made to The Royal Horticultural Society Colour Chart, Fifth Edition, except where general terms of ordinary dictionary significance are used.

Botanical classification: *Camellia sasanqua* 'Green 97-039'.

Parentage:

*Female, or seed, parent.*—*Camellia sasanqua* 'Mine-No-Yuki', not patented.

*Male, or pollen, parent.*—Unknown selection of *Camellia sasanqua*, not patented.

Propagation:

*Type.*—By vegetative cuttings.

*Time to initiate roots, summer.*—About two months at temperatures of 27° C. to 35° C.

*Time to initiate roots, winter.*—About three months at temperatures of 21° C. to 27° C.

*Time to produce a rooted young plant, summer.*—About four months at temperatures of 27° C. to 35° C.

*Time to produce a rooted young plant, winter.*—About five months at temperatures of 21° C. to 27° C.

*Root description.*—Fibrous; close to 164B in color.

*Rooting habit.*—Moderate branching; moderately dense.

Plant description:

*Plant form and growth habit.*—Perennial, evergreen shrub; upright plant habit; vigorous growth habit. Densely foliated; compact, dense and bushy plants. Freely flowering habit with numerous double flowers per plant.

*Branching habit.*—Freely branching habit; about 24 to 30 lateral branches develop per plant. Pinching enhances lateral branch development.

*Plant height, soil level to top of flowers.*—About 71 cm to 91 cm.

*Plant diameter, area of spread.*—About 41 cm.

*Lateral branch description.*—Length: About 13 cm to 20 cm. Diameter: About 3 mm. Internode length: About 2.5 cm to 7.5 cm. Strength: Moderately strong. Texture: Slightly pubescent. Color: Initially, close to N200A; with development, close to 197A.

*Foliage description.*—Arrangement: Alternate, single. Length: About 4.45 cm. Width: About 2.5 cm. Shape: Ovate. Apex: Acute. Base: Obtuse. Margin: Crenate. Venation pattern: Pinnate. Texture, upper and lower surfaces: Smooth, glabrous. Color: Developing leaves, upper surface: Close to N200A. Developing leaves, lower surface: Close to 199A. Fully expanded leaves, upper surface: Close to 147A; venation, close to 146B. Fully expanded leaves, lower surface: Close to 146B; venation, close to 146B.

*Petiole.*—Length: About 5.6 mm. Diameter: About 1.6 mm. Texture, upper and lower surfaces: Smooth, glabrous. Color, upper and lower surfaces: Close to 143B.

Flower description:

*Natural flowering season.*—Plants of the new *Camellia* typically flower from early November until early January in Fairhope, Ala. Flowers not persistent.

*Flower arrangement and appearance.*—Flowers arranged singly at terminals with usually about six to eight flowers and flower buds per apex; freely flowering habit. Flowers face upward or outward. Flowers rotate and rose-like; double flower form with numerous petals and petaloids per flower.

*Postproduction longevity.*—Plants maintain good flower substance for about one week on the plant.

*Fragrance.*—Slightly fragrant; pleasant.

*Flower diameter.*—About 6 cm to 7.5 cm.

*Flower depth.*—About 4 cm.

*Flower bud.*—Length: About 1.75 cm. Diameter: About 1.5 cm. Shape: Ovoid. Color: Close to NN155A; margins, close to N57A.

*Petals/petaloids.*—Arrangement: Double flower form; about 17 to 28 petals and petaloids arranged in multiple whorls. Length: About 1.4 to 5 cm. Width: About 1.4 cm to 3.5 cm. Shape: Obovate to obcordate. Apex: Retuse. Base: Acute to acuminate. Margin: Entire to lobed; undulating. Texture, upper and lower surfaces: Smooth, glabrous; waxy. Color:

When opening and fully opened, upper surface: Close to NN155A; towards the margin, close to 67C and 58B to 58C. When opening and fully opened, lower surface: Close to NN155A; faintly tinted with close to 68B and 58B to 58C.

*Sepals.*—Arrangement: About four to six fused in a single whorl. Length: About 0.5 cm to 1cm. Width: About 7 mm. Shape: Orbicular. Apex: Obtuse. Base: Obtuse. Margin: Entire. Texture, upper surface: Glabrous. Texture, lower surface: Tomentose. Color, upper and lower surfaces: Close to 145B tinted with close to 163A.

*Peduncles.*—Length: About 1 mm. Diameter: About 1 mm to 2 mm. Angle: Upright or outwardly. Strength: Strong. Texture: Glabrous. Color: Close to 144A.

*Reproductive organs.*—Androecium: Quantity per flower: About 36 to 48. Filament length: About 1.5 cm. Filament color: Close to 1D. Anther shape: Oblong. Anther length: About 3 mm to 4 mm. Anther color: Close to 1D. Pollen amount: Moderate. Pollen color: Close to 13B. Gynoecium: Quantity of pistils per flower: Typically one. Pistil length: About 1.5 cm. Style length: About 9 mm. Style color: Close to 145D. Stigma shape: Bi-parted. Stigma color: Close to 145B. Ovary color: Close to 145D.

*Fruits.*—Length: About 1.25 cm. Diameter: About 1.25 cm. Color: Close to N200A.

*Seeds.*—Length: About 1 cm. Diameter: About 1 cm. Color: Close to N200A.

Weather/temperature tolerance: Plants of the new *Camellia* have been observed to be tolerant to rain and wind and to tolerate temperatures from about −23° C. to about 49° C.

Disease/pest resistance: Plants have been observed to be resistant to *Glomerella cingulata*. Plants of the new *Camellia* have not been observed to be resistant to pests and other pathogens common to *Camellias*.

It is claimed:

1. A new and distinct cultivar of *Camellia* plant named 'Green 97-039' as illustrated and described.

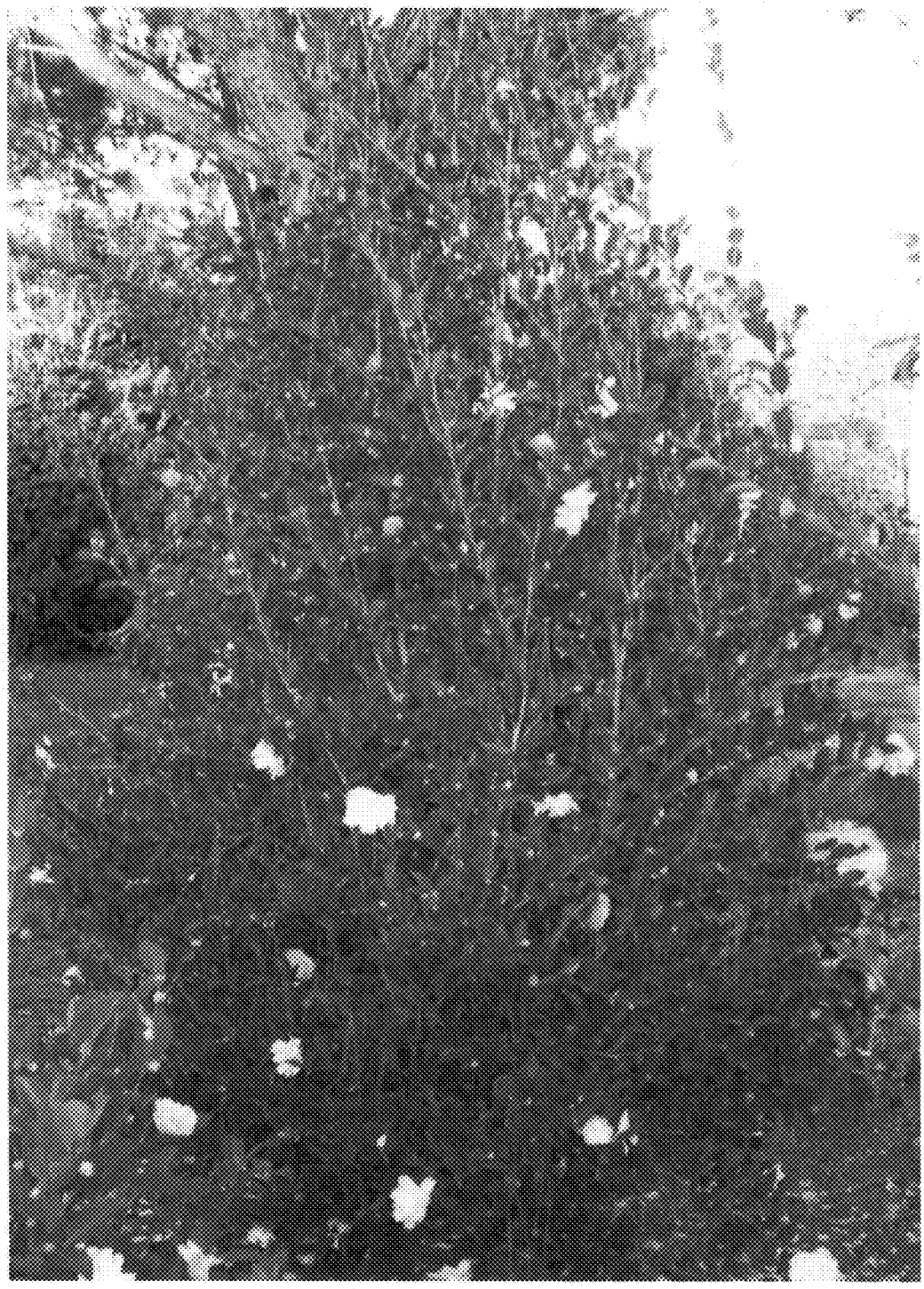

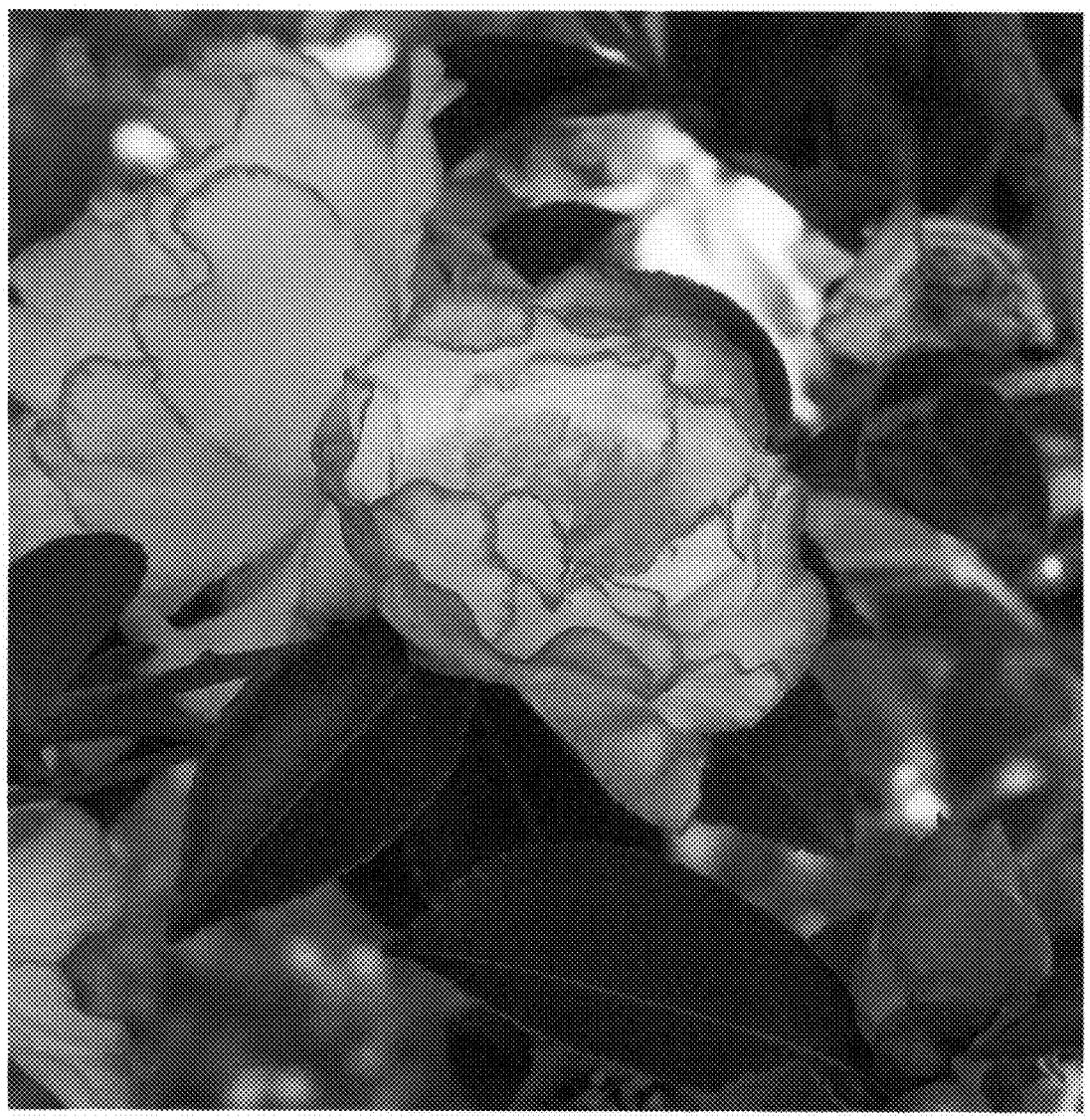

* * * * *